United States Patent
Reinhold et al.

(10) Patent No.: US 11,547,678 B2
(45) Date of Patent: Jan. 10, 2023

(54) AQUEOUS PHARMACEUTICAL FORMULATION OF TAPENTADOL FOR ORAL ADMINISTRATION

(71) Applicant: GRÜNENTHAL GMBH, Aachen (DE)

(72) Inventors: Ulrich Reinhold, Aachen (DE); Marc Schiller, Aachen (DE); Eva Wulsten, Willich (DE); Sabine Karine Katrien Inghelbrecht, Beerse (BE); Roger Carolus Augusta Embrechts, Beerse (BE); Ulrich Feil, Aschaffenburg (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 16/662,392

(22) Filed: Oct. 24, 2019

(65) Prior Publication Data

US 2020/0054584 A1   Feb. 20, 2020

Related U.S. Application Data

(63) Continuation of application No. 15/093,522, filed on Apr. 7, 2016, now abandoned, which is a continuation of application No. 13/410,768, filed on Mar. 2, 2012, now abandoned.

(60) Provisional application No. 61/449,287, filed on Mar. 4, 2011.

(30) Foreign Application Priority Data

May 3, 2011   (EP) .................................. 11003601

(51) Int. Cl.
| A61K 9/08 | (2006.01) |
| A61K 31/137 | (2006.01) |
| A61K 47/12 | (2006.01) |
| A61K 9/00 | (2006.01) |
| A61K 47/02 | (2006.01) |

(52) U.S. Cl.
CPC .......... *A61K 31/137* (2013.01); *A61K 9/0053* (2013.01); *A61K 9/0095* (2013.01); *A61K 9/08* (2013.01); *A61K 47/02* (2013.01); *A61K 47/12* (2013.01)

(58) Field of Classification Search
CPC ............... A61K 9/06; A61K 9/08; A61K 9/10
See application file for complete search history.

(56) References Cited

U.S. PATENT DOCUMENTS

| 4,775,678 | A | 10/1988 | Su et al. |
| 6,183,758 | B1 | 2/2001 | Scott |
| 6,248,737 | B1 | 6/2001 | Buschmann et al. |
| 6,399,087 | B1 | 6/2002 | Zhang et al. |
| 6,638,981 | B2 | 10/2003 | Williams et al. |
| 6,992,218 | B2 | 1/2006 | Dietlin |
| 8,536,130 | B2 | 9/2013 | Christoph et al. |
| 9,446,008 | B2 | 9/2016 | Reinhold et al. |
| 2003/0191187 | A1 | 10/2003 | Lee et al. |
| 2003/0203055 | A1* | 10/2003 | Rao ............................ A61P 1/04 424/738 |
| 2004/0054012 | A1 | 3/2004 | Dietlin et al. |
| 2004/0101263 | A1 | 5/2004 | Kundu et al. |
| 2004/0101563 | A1 | 5/2004 | Kundu et al. |
| 2004/0180915 | A1 | 9/2004 | Gonzales et al. |
| 2005/0058706 | A1 | 3/2005 | Bartholomaeus et al. |
| 2005/0070613 | A1 | 3/2005 | Dinnequin |
| 2005/0176790 | A1 | 8/2005 | Bartholomaus et al. |
| 2005/0186267 | A1* | 8/2005 | Thompson ........... A61K 31/724 424/451 |
| 2006/0039864 | A1 | 2/2006 | Bartholomaus et al. |
| 2006/0051422 | A1 | 3/2006 | Colombo et al. |
| 2006/0111382 | A1 | 5/2006 | Shafer et al. |
| 2007/0128412 | A1 | 6/2007 | Tso et al. |
| 2007/0166336 | A1* | 7/2007 | Delmarre ................. A61P 25/06 424/400 |
| 2007/0213405 | A1 | 9/2007 | Fischer et al. |
| 2008/0039405 | A1 | 2/2008 | Langley et al. |
| 2008/0075790 | A1 | 3/2008 | Kabra et al. |
| 2008/0269326 | A1* | 10/2008 | Christoph ............. A61K 31/137 514/529 |
| 2009/0012180 | A1 | 1/2009 | Lange et al. |
| 2009/0163451 | A1* | 6/2009 | Porreca ................... A61P 29/00 514/165 |
| 2009/0169631 | A1 | 7/2009 | Zamloot et al. |
| 2010/0040559 | A1 | 2/2010 | Leiner et al. |
| 2010/0227921 | A1 | 9/2010 | Franklin et al. |
| 2010/0272815 | A1* | 10/2010 | Khunt ................... C07C 215/54 424/489 |
| 2010/0311842 | A1 | 12/2010 | Christoph et al. |
| 2011/0021426 | A1 | 1/2011 | Toll et al. |
| 2011/0098284 | A1 | 4/2011 | Babul |

(Continued)

FOREIGN PATENT DOCUMENTS

| AU | 2005259478 B2 | 7/2010 |
| CA | 2 725 635 A1 | 9/2002 |

(Continued)

OTHER PUBLICATIONS

U.S. Appl. No. 15/232,841, filed Aug. 10, 2016.
Alfonso, G.R., "Remington Farmacia," p. 2,415 (1998).
GRUENENTHAL GMBH, Ecuadorian Patent Document No. SP-06-7097, dated Dec. 19, 2006.
GRUENENTHAL GMBH, Ecuadorian Patent Document No. SP-06-7117, dated Dec. 26, 2006.
GRUENENTHAL GMBH, Ecuadorian Patent Document No. SP-08-8793, dated Oct. 6, 2008.
GRUENENTHAL GMBH, Ecuadorian Patent Document No. SP-08-8873, dated Nov. 11, 2008.
"Remington Essentials of Pharmaceutics" (Felton, L.A., ed.) Pharmaceutical Press (2013).

(Continued)

*Primary Examiner* — Micah Paul Young
(74) *Attorney, Agent, or Firm* — Norris McLaughlin, P.A.

(57) ABSTRACT

An aqueous pharmaceutical composition containing tapentadol or a physiologically acceptable salt thereof and being adapted for oral administration. The composition has excellent storage stability without relying on the presence of high amounts of preservatives.

13 Claims, No Drawings

(56) References Cited

U.S. PATENT DOCUMENTS

| | | |
|---|---|---|
| 2011/0190267 A1 | 8/2011 | Franklin et al. |
| 2012/0201891 A1 | 8/2012 | Cottrell et al. |
| 2012/0225951 A1 | 9/2012 | Christoph et al. |
| 2012/0270848 A1 | 10/2012 | Mannion et al. |
| 2013/0022670 A1 | 1/2013 | Reinhold et al. |
| 2013/0237608 A1 | 9/2013 | Bartholomaeus et al. |
| 2013/0273152 A1 | 10/2013 | Draget et al. |
| 2016/0106688 A1 | 4/2016 | Christoph et al. |
| 2018/0125800 A1 | 5/2018 | Schiller et al. |
| 2018/0221308 A1 | 8/2018 | Bartholomaeus et al. |
| 2020/0215003 A1 | 7/2020 | Christoph |

FOREIGN PATENT DOCUMENTS

| | | |
|---|---|---|
| CA | 2 572 352 A1 | 1/2006 |
| CA | 2572532 A1 | 1/2006 |
| CA | 2 439 269 C | 11/2011 |
| CN | 101495447 A | 7/2009 |
| CN | 102711726 A | 10/2012 |
| CN | 103501775 A | 1/2014 |
| CN | 103735500 A | 4/2014 |
| EA | 201300988 A1 | 6/2014 |
| EP | 0 147 222 A2 | 7/1985 |
| EP | 0 147 223 A2 | 7/1985 |
| EP | 391369 B1 | 10/1990 |
| EP | 0 693 475 A1 | 1/1996 |
| EP | 1 612 203 B1 | 8/2007 |
| EP | 2 117 525 A1 | 11/2009 |
| JP | S60-156602 A | 8/1985 |
| JP | S 60-156602 A | 8/1985 |
| JP | 2002-316926 A | 10/2002 |
| JP | 2004-516265 A | 6/2004 |
| JP | 2004-527491 A | 9/2004 |
| JP | 2006-512344 A | 4/2006 |
| JP | 2008-266168 A | 11/2008 |
| JP | 2008-539269 A | 11/2008 |
| JP | 2010-520907 A | 6/2010 |
| JP | 2010-536712 A | 12/2010 |
| JP | 2011506342 A | 3/2011 |
| JP | 2013-527152 A | 6/2013 |
| MX | 03007712 A | 3/2004 |
| MX | PA03007712 A | 3/2004 |
| RU | 2 309 942 C2 | 11/2007 |
| WO | 01/22998 A1 | 4/2001 |
| WO | 01/93830 A1 | 12/2001 |
| WO | 02/072080 A2 | 9/2002 |
| WO | WO 02/067651 A2 | 9/2002 |
| WO | WO 02/067916 A2 | 9/2002 |
| WO | 03/041687 A2 | 5/2003 |
| WO | WO 03/035053 A1 | 5/2003 |
| WO | 2004/062689 A1 | 7/2004 |
| WO | WO 2006/002886 A1 | 1/2006 |
| WO | WO 2006/116626 A2 | 11/2006 |
| WO | WO 2006/116626 A3 | 11/2006 |
| WO | WO 2007/128412 A1 | 11/2007 |
| WO | WO 2007/128413 A1 | 11/2007 |
| WO | WO 2008/012283 A1 | 1/2008 |
| WO | WO 2008/110323 A1 | 9/2008 |
| WO | 2008128740 A1 | 10/2008 |
| WO | 2008/135601 A2 | 11/2008 |
| WO | WO 2009/067703 A2 | 5/2009 |
| WO | WO 2009/092601 A1 | 7/2009 |
| WO | 2009/124586 A1 | 10/2009 |
| WO | WO 2010/089767 A1 | 8/2010 |
| WO | WO 2010/096045 A1 | 8/2010 |
| WO | 2010/122442 A1 | 10/2010 |
| WO | WO 2010/122442 A1 | 10/2010 |
| WO | 2011/016487 A1 | 2/2011 |
| WO | WO 2011/016487 A1 | 2/2011 |
| WO | 2011/071400 A1 | 6/2011 |
| WO | WO 2011/128630 A2 | 10/2011 |
| WO | 2012/119727 A1 | 9/2012 |
| WO | 2012/119728 A1 | 9/2012 |
| WO | WO 2012/119729 A1 | 9/2012 |
| WO | 2013/144814 A1 | 10/2013 |
| WO | WO 2014/005546 A1 | 1/2014 |
| WO | WO 2014/191710 A1 | 12/2014 |
| WO | WO 2015/113200 A1 | 8/2015 |
| WO | WO 2016/156147 A1 | 10/2016 |

OTHER PUBLICATIONS

U.S. Appl. No. 16/662,392, filed Oct. 24, 2019.
European Pharmacopoeia 7.0, "5.1.3 Efficacy of Antimicrobial Preservation"; 2011; pp. 505-506.
Fude, Cui; "Pharmacy", People's Medical Publishing House, 2004, p. 59.
Yu et al.; "Newly Edited Manual of Medicines for External Use"; Shandong Science and Technology Press, 1996, p. 54.
U.S. Appl. No. 13/410,768, filed Mar. 2, 2012.
U.S. Appl. No. 15/093,522, filed Apr. 7, 2016.
English translation of Japanese Patent Application No. 2002-316926 A.
Bibliographic information for Japanese Patent Application No. 2004-527491 A.
English translation of Japanese Patent Application No. 2008-266168 A.
Bibliographic data for Japanese Patent Application No. 2010-520907 A.
U.S. Appl. No. 15/867,330, filed Jan. 10, 2018.
Buelbring, E., et al. "Biological Comparison of Local Anaestetics," J. Pharmacol. Exp. Ther. 85:78-41 (1945).
Ramanath Royal, B., "Pharmaceutical Aspects of Tapentadol," Int. J. Pharm. Bioscience 3:79-84 (2012).
U.S. Appl. No. 16/545,567, filed Aug. 20, 2019.
Bibliographic data information for PCT International Publication No. WO 2010/096045 A1.
Bibliographic data information for PCT International Publication No. WO 2011/128630 A2.
U.S. Appl. No. 13/410,945, filed Mar. 2, 2012.
Extended Search Report dated Mar. 23, 2017, and issued in connection with European Patent Application No. 16190255.6.
Extended Search Report dated Aug. 11, 2015, and issued in connection with European Patent Application No. 15169730.7.
Imperfect Gases at http://www4.ncsu.edu/-franzen/public_html/CH433/lecture/Imperfect_Gases_Detail.pdf (retrieved from the Internet on Dec. 13, 2016).
U.S. Appl. No. 15/712,812, filed Sep. 22, 2017.
U.S. Appl. No. 15/867,254, filed Jan. 10, 2018.
Zhang, Q., 2005, pp. 92-117 with partial English Translation (Twenty-eight (28) pages).
Alfonso, G.R., "Remington Farmacia," p. 2,415 (1998) and translation thereof.
Ecuadorian Patent Document No. SP-06-7097, dated Dec. 19, 2006 (related to European Patent No. 1 612 203 B1).
Ecuadorian Patent Document No. SP-06-7117, dated Dec. 26, 2006 (related to U.S. Patent Application Publication No. US 2006/0039864 A1).
Ecuadorian Patent Document No. SP-08-8793, dated Oct. 6, 2008 (related to PCT International Publication No. WO 2007/128413 A1).
Ecuadorian Patent Document No. SP-08-8873, dated Nov. 11, 2008 (related to PCT International Publication No. WO 2007/128412 A1).
U.S. Appl. No. 16/818,275, filed Mar. 13, 2020.
Kumar, R, et al., Development and Characterization of Novel Trans Buccoadhesive Bilayer Tablets of Tapentadol Hydrochloride, Asian Journal of Research in Pharmaceutical Science, vol. 3, Issue, 2 (2013)—Abstract.
Tzschentke et al., "Tapentadol Hydrochloride", Analgesic, Mu-Opioid Receptor Agonist, Noradrenaline Reuptake Inhibitor, Drugs of the Future, vol. 31, No. 12, pp. 1053-1061, Dec. 2006, XP002660111.
Ho et al., "In Vitro Effects Preservatives in Nasal Sprays on Human Nasal Epithelial Cells", American Journal of Rhinology, 2008, vol. 22, No. 2, pp. 125-129.
Hong et al., "Allergy to Ophthalmic Preservatives", Current Opinion in Allergy and Clinical Immunology, 2009, vol. 9, pp. 447-453.

(56) References Cited

OTHER PUBLICATIONS

Soni et al., "Safety Assessment of Propyl Paraben: a Review of the Published Literature", Food and Chemical Toxicology, 2001, vol. 39, No. 6, pp. 513-532.
Oishi, "Effects of Propyl Paraben on the Male Reproductive System", Food and Chemical Toxicology, 2002, vol. 40, No. 12, pp. 1807-1813.
Soni etal., "Safety Assessment of Esters of p-hydroxybenzoic Acid (parabens)", Food and Chemical Toxicology, 2005, vol. 43, No. 7, pp. 985-1015.
European Search Report dated Oct. 12, 2011.
Co-pending U.S. Appl. No. 13/410,945, filed Mar. 2, 2012.
Co-pending U.S. Appl. No. 13/410,837, filed Mar. 2, 2012.
Lippincott et al. (Fluids & Electrolytes—An Incredibly Easy Pocket Guide, (2006), Lippincott, Williams, and Wilkins, Ambler PA, pp. 179-181).
Tamanai-Shacoori et al (2007) "The Antibacterial Activity of Tramadol Against Bacteria Associated with Infectious Complications After Local or Regional Anesthesia." Anesth Analg, 105: 524-27.
Mehta et al (Mar. 20210) "# 228 Tapentadol." Retrieved on 16, Oct. 2014. Retrieved from the Internet <URL: http://www.eperc.mcw.edu/EPERC/FastFactsIndex/ff_228.htm>.
American Academy of Pediatrics (Feb. 2, 1997). "Inactive Ingredients in Pharmaceutical Products: Update (Subject Review)." Pediatrics, 99: 268-278.
Liu, "Pharmacology and clinical application of analgesic tapentadol with a dual mode of action," Pain Clin J., 2008, pp. 293-298, vol. 4, No. 4.
Co-pending U.S. Appl. No. 14/981,223, filed Dec. 28, 2015.
Schroeder, W., et al., "Differential Contribution of Opioid and Noradrenergic Mechanisms of Tapentadol in Rat Models of Nociceptive and Neuropathic Pain", European Journal of Pain, 14, 2010, European Federation of International Association for the Study of Pain Chapters, Published by Elsevier Ltd., pp. 814-821 (Eight (8) pages).
Christoph, T., et al., "Tapentadol, but Not Morphine, Selectively Inhibits Disease-Related Thermal Hyperalgesia in a Mouse Model of Diabetic Neuropathic Pain", Neuroscience Letters, 470, 2010, Elsevier Ireland Ltd., pp. 91-94 (Four (4) pages).

Tzschentke, T., et al., "(-)-(1R, 2R)-3-(3-Dimethylamino-1-ethyl-2-methyl-propyl)-phenol Hydrochloride (Tapentadol HCl): a Novel μ-Opioid Receptor Agonist/Norepinephrine Reuptake Inhibitor with Broad-Spectrum Analgesic Properties", The Journal of Pharmacology and Experimental Therapeutics, 2007, vol. 323, No. 1, pp. 265-276 (Twelve (12) pages).
O'Lenick et al, "Comparatively Speaking: Newtonian vs. Non newtonian Liquids", (https://www.cosmeticsandtoiletries.com/formulating/function/viscositymod/3762622.html) Oct. 13, 2008.
European Search Report dated Sep. 27, 2011 for EP 11003601.
European Search Report dated Jan. 16, 2018 for EP 1719271.
European Search Opinion dated Jan. 16, 2018 for EP 1719271.
European Search Report dated Nov. 25, 2019 for EP 19187973.
European Search Opinion dated Nov. 25, 2019 for EP 19187973.
International Search report dated Jan. 6, 2012 for PCT/EP2012/000905.
International Search report dated Jan. 6, 2012 for PCT/EP2012/000904.
International Preliminary Report on Patentability dated Sep. 10, 2013 for PCT/EP2012/000904.
European Search Reported dated Sep. 27, 2011 for EP 11003602.
European Search Reported dated Feb. 17, 2016 for EP 1520814.
European Search Opinion dated Feb. 17, 2016 for EP 1520814.
International Search Report dated Sep. 10, 2013 for PCT/EP2012/000905.
International Preliminary Report on Patentability dated Sep. 10, 2013 for PCT/EP2012/000905.
De Villiers, "Antimicrobial Preservatives" in Thompson, J.e., et a., "A Practical Guide to Contemporary Pharmacy Practice," 3rd ed., pt. 4, ch. 16, pp. 203-215 (2009).
Merrick, A. Made with love; rose body lotion—Design Sponge, 2010, pp. 1-10.
Preservation Efficacy Test Certificate of Analysis for sodium benzoate 1.5 mg/ml (2020).
Submission dated Jul. 15, 2019, in connection with European Patent Application No. 17 189 271.4.
Maraviroc—Summary of product characteristics.
Notriptyline oral solution—summary of product characteristics.
Rivastigmine oral solution—summary of product characteristics.
Risperidone oral solution—summary of product characteristics.

\* cited by examiner

AQUEOUS PHARMACEUTICAL FORMULATION OF TAPENTADOL FOR ORAL ADMINISTRATION

CROSS REFERENCE TO RELATED APPLICATIONS

This application is a continuation of U.S. patent application Ser. No. 15/093,522, filed Apr. 7, 2016, which is a continuation of U.S. patent application Ser. No. 13/410,768, filed Mar. 2, 2012, now abandoned, which (i) claims the benefit of U.S. Provisional Patent Application No. 61/449,287, filed Mar. 4, 2011; and (ii) European Patent Application No. 11 003 601.9, filed May 3, 2011, the disclosure of each of which is incorporated herein by reference.

BACKGROUND OF THE INVENTION

The invention relates to an aqueous pharmaceutical composition containing tapentadol or a physiologically acceptable salt thereof and being adapted for oral administration.

Tapentadol is a centrally-acting analgesic with a dual mode of action as an agonist at the µ-opioid receptor and as a norepinephrine reuptake inhibitor (cf. T. M. Tzschentke et al., Drugs of the future, 2006, 12, 1053-1061). Solid oral dosage forms of tapentadol are known from the prior art, e.g. WO 02/067651, WO 03/035053, WO 2006/002886, WO 2007/128412, WO 2007/128413, WO 2008/110323, WO 2009/092601, WO 2009/067703, and US 2007-128412.

However, solid oral dosage forms containing tapentadol are not satisfactory in every respect and there is a demand of pharmaceutical formulations which have advantages compared to the known solid oral dosage forms.

The stability of the active ingredient in the final product is a primary concern to the formulator. In general, drug substances are less stable in aqueous media than solid dosage forms, and it is important to properly stabilize and preserve liquid aqueous formulations such as solutions, suspensions, and emulsions. Acid-base reactions, acid or base catalysis, oxidation, and reduction can occur in these products. These reactions can arise from drug substance-ingredient interactions, ingredient-ingredient interactions or container-product interactions. For pH sensitive compounds, any of these interactions may alter the pH and may cause precipitation.

Oxidative labile drug substances or vitamins, essential oils, and almost all fats and oils can be oxidized by auto-oxidation. Such reactions can be initiated by heat, light, peroxides, or other labile compounds or heavy metals such as copper or iron.

The effect of trace metals can be minimized by using chelating agents such as EDTA. Antioxidants may retard or delay oxidation by rapidly reacting with free radicals as they are formed (quenching). Common antioxidants include propyl, octyl and dodecylesters of gallic acid, butylated hydroxyanisole (BHA), butylated hydroxytoluene (BHT), ascorbic acid, sodium ascorbate, monothioglycerol, potassium or sodium metabisulfite, propionic acid, propyl gallate, sodium bisulfite, sodium sulfite, and the tocopherols or vitamin E.

In addition to stabilization of pharmaceutical preparations against chemical and physical degradation, liquid and semi-solid preparations, particularly multiple dosed preparations, must usually be protected against microbial contamination. In contrast to solid preparations, aqueous solutions, syrups, emulsions, and suspensions often provide excellent growth media for microorganisms such as molds, yeast, and bacteria (e.g. *Pseudomonas Aeruginosa, E. Coli, Salmonella* spp., *Staphylococcus aureus, Candida albicans, Aspergillus niger*). Contamination by these microorganisms may occur during manufacturing or when a dose is taken from a multiple dosed formulation. Growth of the microorganisms occurs when a sufficient amount of water is present in the formulation.

Ophthalmic and injectable preparations are typically sterilized by autoclaving or filtration. However, many of them require the presence of an antimicrobial preservative to maintain aseptic conditions throughout their stated shelf life, specifically for multiple dosed preparations.

When a preservative is required, its selection is based upon several considerations, in particular the site of use whether internal, external or ophthalmic (for further details it can be referred to e.g. Remington, The Science and Practice of Pharmacy, $21^{st}$ edition, Lippincott Williams & Wilkins, 2005).

Many liquid formulations for oral administration, particularly multiple dosed formulations, contain parabens as preservatives, e.g. methyl paraben (methyl-4-hydroxybenzoate) and propyl paraben (propyl-4-hydroxybenzoate). For example, in the Federal Republic of Germany liquid oral formulations containing parabens are commercialized under the trademarks: Ben-u-ron®; Cetirizin-ratiopharm®; Pipamperon HEXAL®; Sedotussin®; TALOXA®; Truxal®; XUSAL®; Talvosilen®; and Timonil®. Other commercialized liquid formulations contain sorbic acid or its potassium salt as preservative, e.g. ibuprofen liquid formulations and morphine liquid formulations.

Because of the number of excipients and additives in these preparations, it is recommended all the ingredients be listed on the container to reduce the risks that confront hypersensitive patients when these products are administered.

The preservatives benzalkonium chloride and potassium sorbate are also widely used e.g. in nasal drops and sprays. Recently, side effects resulting from mucosal damage caused by benzalkonium chloride and potassium sorbate were reported (cf. C. Y. Ho et al., Am J Rhinol. 2008, 22(2), 125-9). As far as hypersensitivity reactions of preservatives in topical ophthalmic therapies are concerned, quaternary ammoniums (benzalkonium chloride) are commonly associated with irritant toxic reactions whereas the organomercurials (thimerosal) and the alcohols (chlorobutanol) have high associations, respectively, with allergic responses (cf. J. Hong et al., Curr Opin Allergy Clin Immunol. 2009, 9(5), 447-53). Parabens have been implicated in numerous cases of contact sensitivity associated with cutaneous exposure (cf. M. G. Soni et al., Food Chem Toxicol. 2001, 39(6), 513-32) and have been reported to exert a weak estrogenic activity (cf. S. Oishi, Food Chem Toxicol. 2002, 40(12), 1807-13 and M. G. Soni et al., Food Chem Toxicol. 2005, 43(7), 985-015).

Due to these undesired side effects of known preservatives, it is desirable to provide pharmaceutical compositions for oral administration that exhibit a sufficient shelf life and in use stability in the absence of preservatives or at least in the presence of comparatively low quantities thereof.

WO 2008/110323 discloses a composition for parenteral administration of 20 g (1R,2R)-3-(3-dimethylamino-1-ethyl-2-methyl-propyl)-phenol hydrochloride in 1 L water for injection purposes which has been isotonized by addition of NaCl.

SUMMARY OF THE INVENTION

It is an object of the invention to provide pharmaceutical formulations of tapentadol that have advantages over the pharmaceutical formulations of the prior art. The pharmaceutical formulations should not have the above preservative based side effects that are typically observed with pharmaceutical formulations containing preservatives such as allergic reactions.

This object has been achieved by the invention as described and claimed hereinafter. It has been surprisingly found that tapentadol as such exhibits preservative properties and thus, when formulating comparatively labile compositions, particularly aqueous liquid or semisolid compositions, preservatives can be completely omitted or at least need to be present in comparatively low amounts in order to achieve the stated shelf life.

A first aspect of the invention relates to an aqueous pharmaceutical composition containing tapentadol or a physiologically acceptable salt thereof and being adapted for oral administration.

For the purpose of the specification the term "tapentadol" includes the free base ((1R,2R)-3-(3-dimethylamino-1-ethyl-2-methyl-propyl)-phenol) as well as any physiologically acceptable salt thereof, particularly the hydrochloride ((1R,2R)-3-(3-dimethylamino-1-ethyl-2-methyl-propyl)-phenol hydrochloride). Thus, unless expressly states otherwise, the term "tapentadol" does not only refer to the free base but also to any physiologically acceptable salt. Further, unless expressly stated otherwise, all amounts, contents and concentrations are equivalents related to tapentadol free base.

The composition according to the invention is aqueous. For the purpose of the specification, the term "aqueous" means that its water content is preferably above the typical water content of solid pharmaceutical dosage forms which are humidified from the atmosphere due to the more or less pronounced hygroscopic properties of their constituents.

DETAILED DESCRIPTION OF PREFERRED EMBODIMENTS

Preferably, the water content of the composition is at least 0.5 wt.-%, more preferably at least 1.0 wt.-%, still more preferably at least 2.0 wt.-%, yet more preferably at least 3.0 wt.-%, most preferably at least 4.0 wt.-% and in particular at least 5.0 wt.-%, based on the total weight of the composition.

In a preferred embodiment, the water content of the composition is at least 5 wt.-%, more preferably at least 10 wt.-%, still more preferably at least 20 wt.-%, yet more preferably at least 30 wt.-%, most preferably at least 40 wt.-% and in particular at least 50 wt.-%, based on the total weight of the composition.

In another preferred embodiment, the water content of the composition is within the range of 35±30 wt.-%, more preferably 35±25 wt.-%, still more preferably 35±20 wt.-%, yet more preferably 35±15 wt.-%, most preferably 35±10 wt.-% and in particular 35±5 wt.-%, based on the total weight of the composition.

In another preferred embodiment, the water content of the composition is within the range of 45±30 wt.-%, more preferably 45±25 wt.-%, still more preferably 45±20 wt.-%, yet more preferably 45±15 wt.-%, most preferably 45±10 wt.-% and in particular 45±5 wt.-%, based on the total weight of the composition.

In another preferred embodiment, the water content of the composition is within the range of 55±30 wt.-%, more preferably 55±25 wt.-%, still more preferably 55±20 wt.-%, yet more preferably 55±15 wt.-%, most preferably 55±10 wt.-% and in particular 55±5 wt.-%, based on the total weight of the composition.

In another preferred embodiment, the water content of the composition is within the range of 65±30 wt.-%, more preferably 65±25 wt.-%, still more preferably 65±20 wt.-%, yet more preferably 65±15 wt.-%, most preferably 65±10 wt.-% and in particular 65±5 wt.-%, based on the total weight of the composition.

In another preferred embodiment, the water content of the composition is within the range of 75±24 wt.-%, more preferably 75±22 wt.-%, still more preferably 75±20 wt.-%, yet more preferably 75±15 wt.-%, most preferably 75±10 wt.-% and in particular 75±5 wt.-%, based on the total weight of the composition.

In another preferred embodiment, the water content of the composition is within the range of 85±14 wt.-%, more preferably 85±12 wt.-%, still more preferably 85±10 wt.-%, most preferably 85±7.5 wt.-% and in particular 85±5 wt.-%, based on the total weight of the composition.

In still another preferred embodiment, the water content of the composition is within the range of 95±4.75 wt.-%, more preferably 95±4.5 wt.-%, still more preferably 95±4 wt.-%, yet more preferably 95±3.5 wt.-%, most preferably 95±3 wt.-% and in particular 95±2.5 wt.-%, based on the total weight of the composition.

In a preferred embodiment, the water content of the composition is within the range of from 75 to 99.99 wt.-%, more preferably 80 to 99.98 wt.-%, still more preferably 85 to 99.95 wt.-%, yet more preferably 90 to 99.9 wt.-%, most preferably 95 to 99.7 wt.-% and in particular 96.5 to 99.5 wt.-%, based on the total weight of the composition.

In a preferred embodiment, the composition has a viscosity within the range of 15±12 mPas, more preferably 15±10 mPas, still more preferably 15±8 mPas, yet more preferably 15±6 mPas, most preferably 15±4 mPas, and in particular 15±2 mPas.

In another preferred embodiment, the composition has a viscosity within the range of 30±28 mPas, more preferably 30±20 mPas, still more preferably 30±16 mPas, yet more preferably 30±12 mPas, most preferably 30±8 mPas, and in particular 30±4 mPas.

In still another preferred embodiment, the composition has a viscosity within the range of 60±56 mPas, more preferably 60±40 mPas, still more preferably 60±32 mPas, yet more preferably 60±24 mPas, most preferably 60±16 mPas, and in particular 60±8 mPas.

In yet another preferred embodiment, the composition has a viscosity within the range of 120±112 mPas, more preferably 120±80 mPas, still more preferably 120±64 mPas, yet more preferably 120±48 mPas, most preferably 120±32 mPas, and in particular 120±16 m Pas.

In another preferred embodiment, the composition has a viscosity within the range of 240±224 mPas, more preferably 240±160 mPas, still more preferably 240±128 mPas, yet more preferably 240±96 mPas, most preferably 240±64 mPas, and in particular 240±32 m Pas.

In still another preferred embodiment, the composition has a viscosity within the range of 500±400 mPas, more preferably 500±300 mPas, still more preferably 500±200 mPas, yet more preferably 500±150 mPas, most preferably 500±100 mPas, and in particular 500±50 mPas.

A skilled person knows how to measure the viscosity of pharmaceutical compositions. Preferably, the viscosity is measured at room temperature.

Besides water, the composition according to the invention may contain further solvents.

Further suitable solvents include all physiologically acceptable substances that are normally liquid at ambient or room temperatures. Preferably, the further solvent is water-soluble or water-miscible. Further solvents may be selected from the group consisting of propylene glycol, ethanol, poly(ethylene glycol) or PEG, propylene carbonate, diethylene glycol monoethyl ether, poloxamer, glycofurol, glycerol, and mixtures thereof. Further solvents also include tensides (emulsifiers) and/or fats.

In a preferred embodiment, the composition contains a tenside. In a preferred embodiment, the composition contains a single tenside. In another preferred embodiment, the composition contains a mixture of two or more tensides.

Preferably, the tenside has a hydrophilic-lipophilic balance (HLB) of at least 10. More preferably, the hydrophilic-lipophilic balance (HLB) is at least 12. Most preferably, the hydrophilic-lipophilic balance (HLB) ranges within 14 and 16. The tenside can be an ionic tenside, amphoteric tenside or non-ionic tenside.

In a preferred embodiment, the tenside is ionic, in particular anionic. Suitable anionic ionic tensides include but are not limited to sodium lauryl sulfate (sodium dodecyl sulfate), sodium cetyl stearyl sulfate, sodium dioctylsulfosuccinate (docusate sodium); and the corresponding potassium or calcium salts thereof.

In another preferred embodiment, the tenside is non-ionic. Suitable non-ionic tensides include but are not limited to
  polyoxyethylene-sorbitan-fatty acid esters, e.g. mono- and tri-lauryl, palmityl, stearyl and oleyl esters, such as the type known under the name "polysorbate" and commercially available under the trade name "Tween®" including the tensides tween 20 [polyoxyethylene(20)sorbitan monolaurate], tween 40 [polyoxyethylene(20)sorbitan monopalmitate], 60 [polyoxyethylene(20)sorbitan monostearate], tween 65 [polyoxyethylene(20)sorbitan tristearate], tween 80 [polyoxyethylene(20)sorbitan monooleate], tween 85 [polyoxyethylene(20)sorbitan trioleate], tween 21 [polyoxyethylene(4)sorbitan monolaurate] and tween 81 [polyoxyethylene(5)sorbitan monooleate];
  polyoxyethylene fatty acid esters, the fatty acid preferably having from about 8 to about 18 carbon atoms, e. g. polyoxyethylene esters of 12-hydroxystearic acid, such as the type known and commercially available under the trade name "Solutol®";
  polyoxyethylene esters of alpha-tocopheryl succinate, e. g. D-alpha-tocopheryl-PEG-1000-succinate (TPGS);
  polyglycolyzed glycerides, such as the types known and commercially available under the trade names "Gelucire®" and "Labrasol®";
  reaction products of a natural or hydrogenated castor oil and ethylene oxide such as the various liquid tensides known and commercially available under the trade name "Cremophor®";
  glycerol fatty acid esters, e.g. mono- and tri-lauryl, palmityl, stearyl and oleyl esters, such as for example glyceryl monooleate 40, known and commercially available under the trade name "Peceol®".

Examples of fats include glycerol monostearate, glycerol monopalmitate, stearic acid, diglycol stearate, glycerol trioleate, carnauba wax, bees wax, cetylstearyl alcohol and the like.

Preferably, however, water is the only liquid constituent of the composition according to the invention.

The composition according to the invention is adapted for oral administration. In this regard, oral administration includes every administration through the oral cavity such as peroral, sublingual, buccal, and the like. Preferably, oral administration has the purpose of systemically administering tapentadol upon swallowing.

The term "pharmaceutical composition" includes any pharmaceutical preparation or formulation that is customized for being administered to a human being or animal. Preferably, the composition contains one or more physiologically acceptable carriers, preferably water, and/or excipients. The pharmaceutical composition may be a subunit of a pharmaceutical dosage form, e.g. the liquid core of a capsule.

Preferably, the composition according to the invention is buffered, i.e. contains one or more buffers and buffer systems (i.e. conjugate acid-base-pairs), respectively. Preferred buffer systems are derived from the following acids: organic acids such as acetic acid, propionic acid, maleic acid, fumaric acid, malonic acid, malic acid, mandelic acid, citric acid, tartric acid; or inorganic acids such as phosphoric acid. Citric acid or citric acid monohydrate are particularly preferred. When the buffer systems are derived from any of the above acids, the buffer system constitutes of said acid and its conjugate base.

It has been surprisingly found that the antimicrobial activity of tapentadol depends upon the pH value.

Preferably, the composition has a pH value within the range of from 3.0 to 6.5, more preferably 3.0 to 6.0, still more preferably 3.0 to 5.5, yet more preferably 3.0 to 5.0, most preferably 3.2 to 4.8 and in particular 3.4 to 4.6. Higher pH values are also possible, e.g. 3.0 to 9.0, 3.0 to 8.5, 3.0 to 8.0 or 3.0 to 7.5.

In a preferred embodiment, the composition has a pH value within the range of $3.0\pm1.4$ or $3.0\pm1.3$, more preferably $3.0\pm1.2$ or $3.0\pm1.1$, still more preferably $3.0\pm1.0$ or $3.0\pm0.9$, yet more preferably $3.0\pm0.8$ or $3.0\pm0.7$, even more preferably $3.0\pm0.6$ or $3.0\pm0.5$, most preferably $3.0\pm0.4$ or $3.0\pm0.3$, and in particular $3.0\pm0.2$ or $3.0\pm0.1$.

In a preferred embodiment, the composition has a pH value within the range of $3.5\pm1.4$ or $3.5\pm1.3$, more preferably $3.5\pm1.2$ or $3.5\pm1.1$, still more preferably $3.5\pm1.0$ or $3.5\pm0.9$, yet more preferably $3.5\pm0.8$ or $3.5\pm0.7$, even more preferably $3.5\pm0.6$ or $3.5\pm0.5$, most preferably $3.5\pm0.4$ or $3.5\pm0.3$, and in particular $3.5\pm0.2$ or $3.5\pm0.1$.

In a preferred embodiment, the composition has a pH value within the range of $4.0\pm1.4$ or $4.0\pm1.3$, more preferably $4.0\pm1.2$ or $4.0\pm1.1$, still more preferably $4.0\pm1.0$ or $4.0\pm0.9$, yet more preferably $4.0\pm0.8$ or $4.0\pm0.7$, even more preferably $4.0\pm0.6$ or $4.0\pm0.5$, most preferably $4.0\pm0.4$ or $4.0\pm0.3$, and in particular $4.0\pm0.2$ or $4.0\pm0.1$.

In a preferred embodiment, the composition has a pH value within the range of $4.5\pm1.4$ or $4.5\pm1.3$, more preferably $4.5\pm1.2$ or $4.5\pm1.1$, still more preferably $4.5\pm1.0$ or $4.5\pm0.9$, yet more preferably $4.5\pm0.8$ or $4.5\pm0.7$, even more preferably $4.5\pm0.6$ or $4.5\pm0.5$, most preferably $4.5\pm0.4$ or $4.5\pm0.3$, and in particular $4.5\pm0.2$ or $4.5\pm0.1$.

In a preferred embodiment, the composition has a pH value within the range of $5.0\pm1.4$ or $5.0\pm1.3$, more preferably $5.0\pm1.2$ or $5.0\pm1.1$, still more preferably $5.0\pm1.0$ or $5.0\pm0.9$, yet more preferably $5.0\pm0.8$ or $5.0\pm0.7$, even more preferably $5.0\pm0.6$ or $5.0\pm0.5$, most preferably $5.0\pm0.4$ or $5.0\pm0.3$, and in particular $5.0\pm0.2$ or $5.0\pm0.1$.

In a preferred embodiment, the composition has a pH value within the range of $5.5\pm1.4$ or $5.5\pm1.3$, more preferably $5.5\pm1.2$ or $5.5\pm1.1$, still more preferably $5.5\pm1.0$ or $5.5\pm0.9$, yet more preferably $5.5\pm0.8$ or $5.5\pm0.7$, even more preferably $5.5\pm0.6$ or $5.5\pm0.5$, most preferably $5.5\pm0.4$ or $5.5\pm0.3$, and in particular $5.5\pm0.2$ or $5.5\pm0.1$.

In a preferred embodiment, the composition has a pH value within the range of $6.0\pm1.4$ or $6.0\pm1.3$, more preferably $6.0\pm1.2$ or $6.0\pm1.1$, still more preferably $6.0\pm1.0$ or $6.0\pm0.9$, yet more preferably $6.0\pm0.8$ or $6.0\pm0.7$, even more preferably 6.0±0.6 or 6.0±0.5, most preferably 6.0±0.4 or 6.0±0.3, and in particular 6.0±0.2 or 6.0±0.1.

In a preferred embodiment, the composition has a pH value within the range of 6.5±1.4 or 6.5±1.3, more preferably 6.5±1.2 or 6.5±1.1, still more preferably 6.5±1.0 or 6.5±0.9, yet more preferably 6.5±0.8 or 6.5±0.7, even more preferably 6.5±0.6 or 6.5±0.5, most preferably 6.5±0.4 or 6.5±0.3, and in particular 6.5±0.2 or 6.5±0.1.

In a preferred embodiment, the composition has a pH value within the range of 7.0±1.4 or 7.0±1.3, more preferably 7.0±1.2 or 7.0±1.1, still more preferably 7.0±1.0 or 7.0±0.9, yet more preferably 7.0±0.8 or 7.0±0.7, even more preferably 7.0±0.6 or 7.0±0.5, most preferably 7.0±0.4 or 7.0±0.3, and in particular 7.0±0.2 or 7.0±0.1.

In a preferred embodiment, the composition has a pH value within the range of 7.5±1.4 or 7.5±1.3, more preferably 7.5±1.2 or 7.5±1.1, still more preferably 7.5±1.0 or 7.5±0.9, yet more preferably 7.5±0.8 or 7.5±0.7, even more preferably 7.5±0.6 or 7.5±0.5, most preferably 7.5±0.4 or 7.5±0.3, and in particular 7.5±0.2 or 7.5±0.1.

In a preferred embodiment, the composition has a pH value within the range of 8.0±1.4 or 8.0±1.3, more preferably 8.0±1.2 or 8.0±1.1, still more preferably 8.0±1.0 or 8.0±0.9, yet more preferably 8.0±0.8 or 8.0±0.7, even more preferably 8.0±0.6 or 8.0±0.5, most preferably 8.0±0.4 or 8.0±0.3, and in particular 8.0±0.2 or 8.0±0.1.

In a preferred embodiment, the composition has a pH value within the range of 8.5±1.4 or 8.5±1.3, more preferably 8.5±1.2 or 8.5±1.1, still more preferably 8.5±1.0 or 8.5±0.9, yet more preferably 8.5±0.8 or 8.5±0.7, even more preferably 8.5±0.6 or 8.5±0.5, most preferably 8.5±0.4 or 8.5±0.3, and in particular 8.5±0.2 or 8.5±0.1.

In a preferred embodiment, the composition has a pH value within the range of 9.0±1.4 or 9.0±1.3, more preferably 9.0±1.2 or 9.0±1.1, still more preferably 9.0±1.0 or 9.0±0.9, yet more preferably 9.0±0.8 or 9.0±0.7, even more preferably 9.0±0.6 or 9.0±0.5, most preferably 9.0±0.4 or 9.0±0.3, and in particular 9.0±0.2 or 9.0±0.1.

Preferably, the concentration of the buffer and buffer system, respectively, preferably citric acid or its monohydrate, is adjusted to provide a sufficient buffer capacity.

Preferably, the content of the buffer and buffer system, respectively, preferably citric acid or its monohydrate, is within the range of from 0.0001 to 5.0 wt.-%, more preferably 0.0005 to 4.5 wt.-%, still more preferably 0.001 to 4.0 wt.-%, yet more preferably 0.005 to 3.5 wt.-%, most preferably 0.01 to 3.0 wt.-% and in particular 0.05 to 2.5 wt.-%, based on the total weight of the composition.

In a preferred embodiment, the buffer and buffer system, respectively, preferably citric acid or its monohydrate, has a concentration within the range of 1.0±0.6 mg/mL, more preferably 1.0±0.5 mg/mL, still more preferably 1.0±0.4 mg/mL, yet more preferably 1.0±0.3 mg/mL, most preferably 1.0±0.2 mg/mL, and in particular 1.0±0.1 mg/mL, based on the total volume of the composition.

In another preferred embodiment, the buffer and buffer system, respectively, preferably citric acid or its monohydrate, has a concentration within the range of 1.5±0.6 mg/mL, more preferably 1.5±0.5 mg/mL, still more preferably 1.5±0.4 mg/mL, yet more preferably 1.5±0.3 mg/mL, most preferably 1.5±0.2 mg/mL, and in particular 1.5±0.1 mg/mL, based on the total volume of the composition.

In still another preferred embodiment, the buffer and buffer system, respectively, preferably citric acid or its monohydrate, has a concentration within the range of 2.0±0.6 mg/mL, more preferably 2.0±0.5 mg/mL, still more preferably 2.0±0.4 mg/mL, yet more preferably 2.0±0.3 mg/mL, most preferably 2.0±0.2 mg/mL, and in particular 2.0±0.1 mg/mL, based on the total volume of the composition.

In yet another preferred embodiment, the buffer and buffer system, respectively, preferably citric acid or its monohydrate, has a concentration within the range of 2.5±0.6 mg/mL, more preferably 2.5±0.5 mg/mL, still more preferably 2.5±0.4 mg/mL, yet more preferably 2.5±0.3 mg/mL, most preferably 2.5±0.2 mg/mL, and in particular 2.5±0.1 mg/mL, based on the total volume of the composition.

A skilled person is fully aware that multiprotonic acids can form more than a single buffer system. For example, citric acid is a triprotonic acid so that it forms the conjugate acid-base pairs citric acid-dihydrogencitrate, dihydrogencitrate-hydrogencitrate and hydrogencitrate-citrate. In other words, any of citric acid, dihydrogencitrate and hydrogencitrate can be the acid of a buffer system with the conjugate base. For the purpose of the specification, the expression "buffer and buffer system, respectively" preferably refers to the quantity of both, the acid and its conjugate base. Further, a skilled person is fully aware that a buffer system, e.g. the conjugate system citric acid/sodium dihydrogencitrate can be established either by adding citric acid and an appropriate amount of sodium hydroxide or citric acid and sodium dihydrogencitrate as such.

In a preferred embodiment, the content of tapentadol is within the range of from 0.01 to 50 wt.-%, more preferably 0.05 to 45 wt.-%, still more preferably 0.1 to 40 wt.-%, yet more preferably 0.5 to 35 wt.-%, most preferably 1.0 to 30 wt.-% and in particular 5.0 to 25 wt.-%, based on the total weight of the composition.

In another preferred embodiment, the content of tapentadol is within the range of from 0.0001 to 5.0 wt.-%, more preferably 0.0005 to 4.5 wt.-%, still more preferably 0.001 to 4.0 wt.-%, yet more preferably 0.005 to 3.5 wt.-%, most preferably 0.01 to 3.0 wt.-% and in particular 0.05 to 2.5 wt.-%, based on the total weight of the composition. In a preferred embodiment, the content of tapentadol is within the range of from 0.01 to 3.0 wt.-%, more preferably 0.05 to 2.8 wt.-%, still more preferably 0.1 to 2.6 wt.-%, yet more preferably 0.2 to 2.4 wt.-%, most preferably 0.3 to 2.2 wt.-% and in particular 0.4 to 2.0 wt.-%, based on the total weight of the composition.

Preferably, the concentration of tapentadol is equal or below 200 mg/mL, more preferably equal or below 150 mg/mL, still more preferably equal or below 100 mg/mL, yet more preferably equal or below 75 mg/mL, and most preferably equal or below 50 mg/mL, and in particular equal or below 30 mg/mL, based on the total volume of the composition.

Preferably, the concentration of tapentadol is within the range of from 0.5 to 200 mg/mL, more preferably within the range of from 1.0 to 150 mg/mL, still more preferably within the range of from 1.5 to 100 mg/mL, yet more preferably within the range of from 2.0 to 75 mg/mL, most preferably within the range of from 2.5 to 50 mg/mL, and in particular within the range of from 3.0 to 25 mg/mL based on the total volume of the composition.

In a preferred embodiment, the concentration of tapentadol is equal or below 20 mg/mL, based on the total volume of the composition.

It has been found that the antimicrobial effect of tapentadol, its preservative effect, is a function of the pH value. Thus, at a given pH value a certain minimum concentration of tapentadol is already sufficient in order to achieve the desired preserving effect, while at another pH value another minimum concentration of tapentadol is necessary in order to achieve the same preserving effect. This minimum concentration for a given pH value can be determined by routine experimentation.

In a preferred embodiment, the concentration of tapentadol is within the range of 20±6 mg/mL, more preferably 20±5 mg/mL, still more preferably 20±4 mg/mL, yet more preferably 20±3 mg/mL, most preferably 20±2 mg/mL, and in particular 20±1 mg/mL, based on the total volume of the composition.

In another preferred embodiment, the concentration of tapentadol is within the range of 17.5±6 mg/mL, more preferably 17.5±5 mg/mL, still more preferably 17.5±4 mg/mL, yet more preferably 17.5±3 mg/mL, most preferably 17.5±2 mg/mL, and in particular 17.5±1 mg/mL, based on the total volume of the composition.

In another preferred embodiment, the concentration of tapentadol is within the range of 15±6 mg/mL, more preferably 15±5 mg/mL, still more preferably 15±4 mg/mL, yet more preferably 15±3 mg/mL, most preferably 15±2 mg/mL, and in particular 15±1 mg/mL, based on the total volume of the composition.

In still another preferred embodiment, the concentration of tapentadol is within the range of 12.5±6 mg/mL, more preferably 12.5±5 mg/mL, still more preferably 12.5±4 mg/mL, yet more preferably 12.5±3 mg/mL, most preferably 12.5±2 mg/mL, and in particular 12.5±1 mg/mL, based on the total volume of the composition.

In still another preferred embodiment, the concentration of tapentadol is within the range of 10±6 mg/mL, more preferably 10±5 mg/mL, still more preferably 10±4 mg/mL, yet more preferably 10±3 mg/mL, most preferably 10±2 mg/mL, and in particular 10±1 mg/mL, based on the total volume of the composition.

In yet another preferred embodiment, the concentration of tapentadol is within the range of 7.5±6 mg/mL, more preferably 7.5±5 mg/mL, still more preferably 7.5±4 mg/mL, yet more preferably 7.5±3 mg/mL, most preferably 7.5±2 mg/mL, and in particular 7.5±1 mg/mL, based on the total volume of the composition.

In a further preferred embodiment, the concentration of tapentadol is within the range of 4±3 mg/mL, more preferably 4±2.5 mg/mL, still more preferably 4±2 mg/mL, yet more preferably 4±1.5 mg/mL, most preferably 4±1 mg/mL, and in particular 4±0.5 mg/mL, based on the total volume of the composition.

In another preferred embodiment, the concentration of tapentadol is equal or above 20 mg/mL, based on the total volume of the composition.

In a preferred embodiment, the concentration of tapentadol is within the range of 22.5±6 mg/mL, more preferably 22.5±5 mg/mL, still more preferably 22.5±4 mg/mL, yet more preferably 22.5±3 mg/mL, most preferably 22.5±2 mg/mL, and in particular 22.5±1 mg/mL, based on the total volume of the composition.

In another preferred embodiment, the concentration of tapentadol is within the range of 25±6 mg/mL, more preferably 25±5 mg/mL, still more preferably 25±4 mg/mL, yet more preferably 25±3 mg/mL, most preferably 25±2 mg/mL, and in particular 25±1 mg/mL, based on the total volume of the composition.

In another preferred embodiment, the concentration of tapentadol is within the range of 27.5±6 mg/mL, more preferably 27.5±5 mg/mL, still more preferably 27.5±4 mg/mL, yet more preferably 27.5±3 mg/mL, most preferably 27.5±2 mg/mL, and in particular 27.5±1 mg/mL, based on the total volume of the composition.

In still another preferred embodiment, the concentration of tapentadol is within the range of 30±6 mg/mL, more preferably 30±5 mg/mL, still more preferably 30±4 mg/mL, yet more preferably 30±3 mg/mL, most preferably 30±2 mg/mL, and in particular 30±1 mg/mL, based on the total volume of the composition.

In still another preferred embodiment, the concentration of tapentadol is within the range of 32.5±6 mg/mL, more preferably 32.5±5 mg/mL, still more preferably 32.5±4 mg/mL, yet more preferably 32.5±3 mg/mL, most preferably 32.5±2 mg/mL, and in particular 32.5±1 mg/mL, based on the total volume of the composition.

In yet another preferred embodiment, the concentration of tapentadol is within the range of 35±6 mg/mL, more preferably 35±5 mg/mL, still more preferably 35±4 mg/mL, yet more preferably 35±3 mg/mL, most preferably 35±2 mg/mL, and in particular 35±1 mg/mL, based on the total volume of the composition.

In a preferred embodiment, the composition does not contain any preservative. For the purpose of the specification, a "preservative" preferably refers to any substance that is usually added to pharmaceutical compositions in order to preserve them against microbial degradation or microbial growth. In this regard, microbial growth typically plays an essential role, i.e. the preservative serves the main purpose of avoiding microbial contamination. As a side aspect, it may also be desirable to avoid any effect of the microbes on the active ingredients and excipients, respectively, i.e. to avoid microbial degradation.

Representative examples of preservatives include benzalkonium chloride, benzethonium chloride, benzoic acid, sodium benzoate, benzyl alcohol, bronopol, cetrimide, cetylpyridinium chloride, chlorhexidine, chlorbutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, sodium propionate, thimerosal, methyl paraben, ethyl paraben, propyl paraben, butyl paraben, isobutyl paraben, benzyl paraben, sorbic acid, and potassium sorbate. Sodium benzoate is particularly preferred.

The complete absence of preservatives in the composition is preferred when the content of tapentadol is sufficiently high so that due to its preservative property the desired shelf life or in use stability can be achieved by the presence of the drug itself. Preferably, under these circumstances the concentration of tapentadol is at least 10 mg/mL, at least 12.5 mg/mL, at least 15 mg/mL, or at least 17.5 mg/mL, based on the total volume of the composition.

The complete absence of preservatives in the composition is also preferred when the pH value of the aqueous composition is sufficiently high so that due to its preservative property the desired shelf life or in use stability can be achieved by the presence of the drug itself. Preferably, under these circumstances the pH value of the composition is at least 3.0, at least 3.5, at least 4.0, or at least 4.5 mg/mL.

For the purpose of the specification, it is preferably distinguished between shelf life and in-use stability. Shelf life preferably refers to the storage stability of a closed container of the pharmaceutical composition. In-use stability preferably refers to the storage container that contains a multiple dose preparation which has been utilized for the first time. Typically, the shelf-life of a multiple dose preparation is much longer than its in-use stability.

In another preferred embodiment, the composition additionally contains a preservative, which is preferably selected from the group consisting of benzalkonium chloride, benzethonium chloride, benzoic acid, sodium benzoate, benzyl alcohol, bronopol, cetrimide, cetylpyridinium chloride, chlorhexidine, chlorbutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, sodium propionate, thimerosal, methyl paraben, ethyl paraben, propyl paraben, butyl paraben, isobutyl paraben, benzyl paraben, sorbic acid, and potassium sorbate.

It has been surprisingly found that aqueous tapentadol compositions containing sodium benzoate show a lower decrease in preservative at 50° C. and less degradation products compared with aqueous tapentadol compositions containing parabens. Thus, sodium benzoate is a particularly preferred preservative according to the invention.

Preferably, the content of the preservative is at most 5.0 wt.-%, more preferably at most 4.0 wt.-%, still more preferably at most 3.0 wt.-%, yet more preferably at most 2.0 wt.-%, most preferably at most 1.0 wt.-% and in particular at most 0.5 wt.-%, based on the total weight of the composition.

In a preferred embodiment, the preservative, preferably benzoic acid or its sodium salt, has a concentration within the range of 1.0±0.6 mg/mL, more preferably 1.0±0.5 mg/mL, still more preferably 1.0±0.4 mg/mL, yet more preferably 1.0±0.3 mg/mL, most preferably 1.0±0.2 mg/mL, and in particular 1.0±0.1 mg/mL, based on the total volume of the composition.

In another preferred embodiment, the preservative, preferably benzoic acid or its sodium salt, has a concentration within the range of 1.5±0.6 mg/mL, more preferably 1.5±0.5 mg/mL, still more preferably 1.5±0.4 mg/mL, yet more preferably 1.5±0.3 mg/mL, most preferably 1.5±0.2 mg/mL, and in particular 1.5±0.1 mg/mL, based on the total volume of the composition.

In still another preferred embodiment, the preservative, preferably benzoic acid or its sodium salt, has a concentration within the range of 2.0±0.6 mg/mL, more preferably 2.0±0.5 mg/mL, still more preferably 2.0±0.4 mg/mL, yet more preferably 2.0±0.3 mg/mL, most preferably 2.0±0.2 mg/mL, and in particular 2.0±0.1 mg/mL, based on the total volume of the composition.

In yet another preferred embodiment, the preservative, preferably benzoic acid or its sodium salt, has a concentration within the range of 2.5±0.6 mg/mL, more preferably 2.5±0.5 mg/mL, still more preferably 2.5±0.4 mg/mL, yet more preferably 2.5±0.3 mg/mL, most preferably 2.5±0.2 mg/mL, and in particular 2.5±0.1 mg/mL, based on the total volume of the composition.

The additional presence of a preservative in the composition is preferred when the content of tapentadol is too low so that due to its preservative property the desired shelf life or in use stability cannot be achieved by the presence of the drug itself. As already mentioned above, the preservative property of tapentadol is a function of the pH value and thus, at one pH value the addition of another preservative might be necessary, whereas at another pH value it can be completely omitted. Preferably, under these circumstances the concentration of tapentadol is at most 12.5 mg/mL, at most 10 mg/mL, at most 8 mg/mL, at most 7.5 mg/mL, at most 5.0 mg/mL, at most 4.0 mg/mL, at most 3.0 mg/mL or at most 2.5 mg/mL, based on the total volume of the composition.

In a preferred embodiment, the relative weight ratio of tapentadol to the preservative is within the range of from 10:1 to 0.25:1, more preferably 9:1 to 0.33:1, still more preferably 8:1 to 0.5:1, yet more preferably 7:1 to 0.66:1, most preferably 6:1 to 0.75:1 and in particular 5:1 to 1:1. Preferably, the relative weight ratio of tapentadol to the preservative is within the range of from 5:1 to 1:1, more preferably 4.5:1 to 1:1, still more preferably 4:1 to 1:1, yet more preferably 3.5:1 to 1:1, most preferably 3:1 to 1:1 and in particular 2.5:1 to 1:1.

Preferably, the sum of the concentration of tapentadol and the concentration of preservative is equal or below 50 mg/mL, preferably equal or below 20 mg/mL, based on the total volume of the composition.

In a preferred embodiment, the sum of the concentration of tapentadol and the concentration of preservative is within the range of 4.0±3.5 mg/mL, more preferably 4.0±3.0 mg/mL, still more preferably 4.0±2.5 mg/mL, yet more preferably 4.0±2.0 mg/mL, most preferably 4.0±1.5 mg/mL, and in particular 4.0±1.0 mg/mL, based on the total volume of the corn position.

In another preferred embodiment, the sum of the concentration of tapentadol and the concentration of preservative is within the range of 6.0±3.5 mg/mL, more preferably 6.0±3.0 mg/mL, still more preferably 6.0±2.5 mg/mL, yet more preferably 6.0±2.0 mg/mL, most preferably 6.0±1.5 mg/mL, and in particular 6.0±1.0 mg/mL, based on the total volume of the corn position.

In still another preferred embodiment, the sum of the concentration of tapentadol and the concentration of preservative is within the range of 8.0±3.5 mg/mL, more preferably 8.0±3.0 mg/mL, still more preferably 8.0±2.5 mg/mL, yet more preferably 8.0±2.0 mg/mL, most preferably 8.0±1.5 mg/mL, and in particular 8.0±1.0 mg/mL, based on the total volume of the composition.

In a preferred embodiment, the content of the preservative is at most 90%, more preferably at most 80%, still more preferably at most 70%, yet more preferably at most 60%, most preferably at most 50% and in particular at most 40% of the content that would be needed according to Ph. Eur. in order to sufficiently preserve the pharmaceutical composition in the absence of tapentadol, either concerning its shelf-life or, in case of multiple dosed preparations, optionally concerning its in-use stability. Sufficient preservation according to Ph. Eur. is preferably defined as in the experimental section (e.g. for molds and yeasts log reduction of 1 after 14 and no increase after 28 days).

Preferably, the composition according to the invention exhibits an antimicrobial robustness that complies with the requirements of the Ph. Eur., preferably in its version for 2010. Preferably, antimicrobial robustness is achieved against E. coli, S. aureus, Ps. aeruginosa, S. spp., C. albicans, and/or A. niger, preferably satisfying the requirement of log reduction of 1 after 14 and no increase after 28 days. In a particularly preferred embodiment, antimicrobial robustness is achieved against bacteria satisfying the requirement of log reduction of 3 after 14 days and against molds and yeast of log reduction of 1 after 14 days.

Preferably, the composition according to the invention exhibits a shelf-life under accelerated storage conditions of at least 1 month, more preferably at least 2 months, still more preferably at least 3 months, yet more preferably at least 4 months, most preferably at least 5 months and in particular at least 6 months. Preferably, the shelf life is determined according to Ph. Eur., particularly as described in the experimental section. Accelerated storage conditions preferably mean 40° C./75% relative humidity.

Preferably, the composition according to the invention exhibits a shelf-life under ambient conditions of at least 6 month, more preferably at least 12 months, still more preferably at least 15 months, yet more preferably at least 18 months, most preferably at least 21 months and in particular at least 24 months.

Preferably, the composition according to the invention is a multiple dosed preparation that exhibits an in-use stability under ambient conditions of at least 1 week, more preferably at least 2 weeks, still more preferably at least 3 weeks, yet more preferably at least 4 weeks, most preferably at least 5 weeks and in particular at least 6 weeks.

Preferably, the composition according to the invention is liquid or semisolid.

Preferably, the composition according to the invention is selected from the group consisting of syrups, drops, solutions, dispersions, suspensions and emulsions. Emulsions may be of o/w-type (oil-in-water) or w/o-type (water-in-oil).

When the pharmaceutical composition is a solution, it may be selected from the group consisting of aromatic waters, aqueous acids, diluted acids, douches, enemas, gargles, mouthwashes, juices, and irrigation solutions.

Preferably, the composition belongs to the group of sweet and other viscid aqueous solutions encompassing syrups, honeys, mucilages, and jellies.

Other examples of compositions according to the invention include collodions, elixirs, glycerins, liniments and spirits.

In a preferred embodiment, the composition according to the invention is an emulsion, preferably selected from the group consisting of conventional emulsions, multiple emulsions, microemulsions and liposomes.

In another preferred embodiment, the composition according to the invention is a suspension, preferably selected from the group consisting of sustained release suspensions, gels and magmas, and lotions.

Preferably, the composition is a multiple dosed form, i.e. customized for more than a single administration. For the purpose of the specification "multiple dosed" preferably means that the composition encompasses more than a single dosage unit. For example, when the composition is a multiple dosed oral solution, its overall volume is more than the volume that is to be typically orally administered at once. Instead, the multiple dosed oral solution is customized for being divided into a multitude of dosage units that are to be administered over a treatment interval typically encompassing several days. For example, when the multiple dosed oral dosage form that is contained in a storage container has a total volume of 250 mL and the prescribed dosage unit is 25 mL once daily, at day 1 of the treatment interval the patient takes 25 mL so that 225 mL remain in the storage container; at day 2 of the treatment interval the patient takes another 25 mL so that 200 mL remain in the storage container; and so on, until at day 10 the entire amount is taken by the patient.

In a preferred embodiment the composition according to the invention is ready to use, i.e. does not require particular treatment steps such as dissolution in a solvent before it may be orally administered to the patient.

A skilled person recognizes that the aqueous composition according to the invention may alternatively be commercialized as a precursor in form of a dry powder that is to be dissolved or dispersed in an appropriate amount of water prior to the first use.

Preferably, the composition according to the invention additionally comprises a taste-enhancing component.

In a preferred embodiment, the taste-enhancing component comprises at least one sweetener, preferably selected from the group comprising cyclamate (E 952), saccharin (E 954) or sodium saccharin, aspartame (E 951), sucralose (E 955), neotame, thaumatine (E 957), neohesperidine (E 959), acesulphame potassium (acesulphame K, E 950) and acesulphame-aspartame salt (E 962), and sorbitol (E 420). Sucralose is particularly preferred.

Preferably, the content of the sweetener amounts to preferably ≤20% by wt., more preferably ≤15% by wt., still more preferably ≤10% by wt., most preferably ≤5.0% by wt., and in particular ≤1.0%, based on the total weight of the composition.

In a preferred embodiment, the concentration of the sweetener, preferably sucralose, is within the range of 2.0±1.5 mg/mL, more preferably 2.0±1.25 mg/mL, still more preferably 2.0±1.0 mg/mL, yet more preferably 2.0±0.75 mg/mL, most preferably 2.0±0.5 mg/mL, and in particular 2.0±0.25 mg/mL, based on the total volume of the composition.

In a preferred embodiment, the concentration of the sweetener, preferably sucralose, is within the range of 2.5±1.5 mg/mL, more preferably 2.5±1.25 mg/mL, still more preferably 2.5±1.0 mg/mL, yet more preferably 2.5±0.75 mg/mL, most preferably 2.5±0.5 mg/mL, and in particular 2.5±0.25 mg/mL, based on the total volume of the composition.

In a preferred embodiment, the taste-enhancing component comprises at least one flavoring agent. Flavoring agents are known to the person skilled in the art. In this context, reference can be made, for example, to the European Commission: *Decision of the Commission concerning a register of flavouring agents used in or on foodstuffs*, of 23 Feb. 1999; last consolidated version dated 29 Mar. 6. Natural or nature-identical flavorings of fruit are particularly preferred. Examples of suitable flavoring agents are orange flavor, blood orange flavor, lemon flavor, lime flavor, grapefruit flavor, strawberry flavor, raspberry flavor, blackcurrant flavor, redcurrant flavor, pineapple flavor, blueberry flavor, cherry flavor, woodruff flavor, vanilla flavor and mixtures thereof, such as wild berry flavor or strawberry-vanilla flavor. Raspberry flavor is particularly preferred.

In a preferred embodiment, the concentration of the flavoring agent, preferably raspberry flavor, is within the range of 2.0±1.5 mg/mL, more preferably 2.0±1.25 mg/mL, still more preferably 2.0±1.0 mg/mL, yet more preferably 2.0±0.75 mg/mL, most preferably 2.0±0.5 mg/mL, and in particular 2.0±0.25 mg/mL, based on the total volume of the composition.

The compositions may include one or more further excipients selected from the group comprising wetting agents, emulsifying agents, isotonizing agents, surfactant components, solubilizing agents, thickening agents, colorant agents, and antioxidant components.

A wetting agent or surfactant component can be included in the liquid compositions of the present invention that, when used, includes one or more quaternary ammonium compounds, such as benzalkonium chloride, benzethonium chloride and cetylpyridinium chloride; TPGS, dioctyl sodium sulfosuccinate; polyoxyethylene alkylphenyl ethers, such as nonoxynol 9, nonoxynol 10, and octoxynol 9; poloxamers (polyoxyethylene and polyoxypropylene block copolymers); polyoxyethylene fatty acid glycerides and oils, such as polyoxyethylene (8) caprylic/capric mono- and diglycerides, polyoxyethylene (35) castor oil and polyoxyethylene (40) hydrogenated castor oil; polyoxyethylene alkyl ethers, such as polyoxyethylene (20) cetostearyl ether; polyoxyethylene fatty acid esters, such as polyoxyethylene (40) stearate; polyoxyethylene sorbitan esters, such as polysorbate 20 and polysorbate 80; propylene glycol fatty acid esters, such as propylene glycol laureate; sodium lauryl sulfate; fatty acids and salts thereof, such as oleic acid, sodium oleate and triethanolamine oleate; glyceryl fatty acid esters, for example glyceryl monostearate; sorbitan esters, such as sorbitan monolaurate, sorbitan monooleate, sorbitan monopalmitate and sorbitan monostearate; tyloxapol; lecithin; stearyl triethanolamine; laurylaminopropionic acid; and mixtures thereof. Such surfactant component or wetting agent, if present, will typically together form about 0.25 wt.-% to about 15 wt.-%, preferably about 0.4 wt.-% to about 10 wt.-%, and more preferably about 0.5 wt.-% to about 5 wt.-%, of the total weight of the corn position.

A thickening agent or viscosity-enhancing agent can be included to generally thicken the liquid composition, which typically improves the mouth-feel of the composition, and/ or to help coat the lining of the gastrointestinal tract. While any suitable thickening agent can be included in the compositions of the present invention, a preferred thickening agent, when used, includes one or more of acacia, alginic acid bentonite, carbomer, carboxymethylcellulose calcium or sodium, cetostearyl alcohol, methyl cellulose, ethylcellulose, glycerin, gelatin guar gum, hydroxyethylcellulose, hydroxypropylcellulose, hydroxypropylmethylcellulose, maltodextrin, polyvinyl alcohol, povidone, propylene carbonate, propylene glycol alginate, sodium alginate, sodium starch glycolate, starch tragacanth, and xanthan gum, and any combination thereof. More preferred thickening agents are glycerin, hydroxypropylmethylcellulose, and xanthan gum, and any combination thereof. Such a thickening agent, if present, will typically form about 0.1 wt.-% to 20 wt.-%, preferably about 0.3 wt.-% to about 15 wt.-%, and more preferably about 0.5 wt.-% to 4 wt.-%, of the total weight of the composition.

A colorant agent, when included, can provide the compositions with a more aesthetic and/or distinctive appearance. Colorant agents preferable for inclusion in the present invention include one or more water-soluble synthetic organic food additives (e.g., food dyes such as food red dye Nos. 2 and 3, food yellow dye Nos. 4 and 5 and food blue dye Nos. 1 and 2), water-insoluble lake dyes (e.g., aluminum salts of the above water-soluble synthetic organic food additives, etc.), and natural pigments (e.g., beta-carotene, chlorophyll, iron oxide red, etc.). Such a colorant agent, if present, will typically form about 0.001 wt.-% to about 1 wt.-%, preferably about 0.001 wt.-% to about 0.5 wt.-%, and more preferably about 0.0075 wt.-% to about 0.25 wt.-%, of the total weight of the composition.

Examples of a suitable antioxidant component, if used, include one or more of the following: sulfites; ascorbic acid; ascorbates, such as sodium ascorbate, calcium ascorbate, or potassium ascorbate; ascorbyl palmitate; fumaric acid; ethylene diamine tetraacetic acid (EDTA) or its sodium or calcium salts; tocopherol; gallates, such as propyl gallate, octyl gallate, or dodecyl gallate; vitamin E; and mixtures thereof. The antioxidant component provides long term stability to the liquid compositions. Addition of the antioxidant component can help enhance and ensure the stability of the compositions and renders the compositions stable even after six months at 40° C. A suitable amount of the antioxidant component, if present, is about 0.01 wt.-% to about 3 wt.-%, preferably about 0.05 wt.-% to about 2 wt.-%, of the total weight of the composition.

Solubilizing and emulsifying agents can be included to facilitate more uniform dispersion of the active ingredient or other excipient that is not generally soluble in the liquid carrier. Examples of a suitable emulsifying agent, if used, includes, for example, gelatin, egg yolk, casein, cholesterol, acacia, tragacanth, chondrus, pectin, methyl cellulose, carbomer, cetostearyl alcohol, cetyl alcohol, and mixtures thereof. Examples of a suitable solubilizing agent include glycol, glycerin, D-mannitol, trehalose, benzyl benzoate, ethanol, trisaminomethane, cholesterol, triethanolamine, sodium carbonate, sodium citrate, sodium salicylate, sodium acetate, and mixtures thereof. Preferably, the solubilizing agent includes glycerin. The solubilizing or emulsifying agent is/are generally present in an amount sufficient to dissolve or disperse the active ingredient, i.e. tapentadol, in the carrier. Typical amounts when a solubilizing or an emulsifier are included are from about 1 wt.-% to about 80 wt.-%, preferably about 20 wt.-% to about 65 wt.-%, and more preferably about 25 wt.-% to about 55 wt.-%, of the total weight of the composition.

A suitable isotonizing agent, if used, includes sodium chloride, glycerin, D-mannitol, D-sorbitol, glucose, and mixtures thereof. A suitable amount of the isotonizing agent, when included, is typically about 0.01 wt.-% to about 15 wt.-%, more preferably about 0.3 wt.-% to about 4 wt.-%, and more preferably about 0.5 wt.-% to about 3 wt.-%, of the total weight of the composition.

Particularly preferred embodiments $E^1$ to $E^8$ of compositions according to the invention are summarized in the following table

|  | $E^1$ | $E^2$ | $E^3$ | $E^4$ |
| --- | --- | --- | --- | --- |
| tapentadol | ≤50 mg/mL | ≤50 mg/mL | ≤30 mg/mL | ≤30 mg/mL |
| buffer | optional | 0.001-4.0 wt. % | 0.05-2.5 wt. % | 0.05-2.5 wt. % |
| preservative | 0-5.0 wt. % | 0-3.0 wt. % | 0-1.0 wt. % | — |
| taste-enhancing component | optional | sweetener and/or flavoring agent | ≤1.0 wt. % sweetener and ≤1.0 wt. % flavoring agent | 2.0 ± 1.5 mg/mL sweetener and 2.0 ± 1.5 mg/mL flavoring agent |
| water | ≥5 wt. % | ≥50 wt. % | 85-99.5 wt. % | 90-99.9 wt. % |

|  | $E^5$ | $E^6$ | $E^7$ | $E^8$ |
| --- | --- | --- | --- | --- |
| tapentadol | ≤20 mg/mL | ≤25 mg/mL | 20 ± 5 mg/mL | 1-10 mg/mL |
| buffer | 0.05-2.5 wt. % | 0.05-1.0 wt. % citric acid or its monohydrate | 2.0 ± 0.6 mg/mL citric acid or its monohydrate | 2.0 ± 0.6 mg/mL citric acid or its monohydrate |
| preservative | 0.01-0.5 wt. % | 0-0.5 wt. % sodium benzoate | — | 2.5 ± 0.5 mg/mL sodium benzoate |
| taste-enhancing component | 2.0 ± 1.5 mg/mL sweetener and 2.0 ± 1.5 mg/mL flavoring agent | 2.0 ± 1.5 mg/mL sucralose and 2.0 ± 1.5 mg/mL flavoring agent | 2.0 ± 1.0 mg/mL sucralose and 2.0 ± 1.0 mg/mL raspberry flavor | 2.0 ± 1.0 mg/mL sucralose and 2.0 ± 1.0 mg/mL raspberry flavor |
| water | 90-99.9 wt. % | 90-99.9 wt. % | 98 ± 1.5 wt. % | 98 ± 1.5 wt. % |

Other particularly preferred embodiments $F^1$ to $F^8$ of compositions according to the invention are summarized in the following table:

|  | $F^1$ | $F^2$ | $F^3$ | $F^4$ |
|---|---|---|---|---|
| tapentadol | 4.7 ± 4.2 mg/mL | 4.7 ± 2.1 mg/mL | 4.7 ± 4.2 mg/mL | 4.7 ± 2.1 mg/mL |
| buffer (pH 3.5-4.5) | 1.7 ± 1.5 mg/mL citric acid or its monohydrate | 1.7 ± 0.8 mg/mL citric acid or its monohydrate | 1.7 ± 1.5 mg/mL citric acid or its monohydrate | 1.7 ± 0.8 mg/mL citric acid or its monohydrate |
| preservative | 2.4 ± 2.0 mg/mL | 2.4 ± 1.0 mg/mL | 2.4 ± 2.0 mg/mL sodium benzoate | 2.4 ± 1.0 mg/mL sodium benzoate |
| taste-enhancing component | 2.0 ± 1.7 mg/mL sweetener and 2.0 ± 1.7 mg/mL flavoring agent | 2.0 ± 0.8 mg/mL sweetener and 2.0 ± 0.8 mg/mL flavoring agent | 2.0 ± 1.7 mg/mL sucralose and 2.0 ± 1.7 mg/mL flavoring agent | 2.0 ± 0.8 mg/mL sucralose and 2.0 ± 0.8 mg/mL flavoring agent |
| water | 90-99.9 wt.-% | 90-99.9 wt.-% | 90-99.9 wt.-% | 90-99.9 wt.-% |

|  | $F^5$ | $F^6$ | $F^7$ | $F^8$ |
|---|---|---|---|---|
| tapentadol | 23.3 ± 18.0 mg/mL | 23.3 ± 9.0 mg/mL | 23.3 ± 18.0 mg/mL | 23.3 ± 9.0 mg/mL |
| buffer (pH 3.5-4.5) | 2.0 ± 1.7 mg/mL citric acid or its monohydrate; and 0.5 ± 0.3 mg/ml alkali hydroxide | 2.0 ± 0.8 mg/mL citric acid or its monohydrate; and 0.5 ± 0.2 mg/ml alkali hydroxide | 2.0 ± 1.7 mg/mL citric acid or its monohydrate; and 0.5 ± 0.3 mg/ml alkali hydroxide | 2.0 ± 0.8 mg/mL citric acid or its monohydrate; and 0.5 ± 0.2 mg/ml alkali hydroxide |
| preservative | — | — |  |  |
| taste-enhancing component | 2.5 ± 2.0 mg/mL sweetener and 2.0 ± 1.7 mg/mL flavoring agent | 2.5 ± 1.0 mg/mL sweetener and 2.0 ± 0.8 mg/mL flavoring agent | 2.5 ± 2.0 mg/mL sucralose and 2.0 ± 1.7 mg/mL flavoring agent | 2.5 ± 1.0 mg/mL sucralose and 2.0 ± 0.8 mg/mL flavoring agent |
| water | 90-99.9 wt.-% | 90-99.9 wt.-% | 90-99.9 wt.-% | 90-99.9 wt.-% |

A further aspect of the invention relates to a pharmaceutical dosage form comprising the pharmaceutical composition according to the invention. All preferred embodiments that are described above in connection with the composition according to the invention also apply to the dosage form according to the invention.

Preferably, the dosage form is selected from the group consisting of oral solutions, oral gels, suspensions, emulsions, liquid or gel filled capsules, liquid-filled lozenges, metered liquid dosing devices, atomizers, nebulizers, sprays, and liquid-releasing, edible capsules.

Compared to solid dosage forms, liquid dosage forms have several advantages. They can be exactly dose, e.g. according to the body weight of the patients, which can be particularly important in pediatric patients. Further, they can be administered by means of probes, e.g. when the patient is young or has problems to swallow.

Furthermore, liquid dosage forms tend to have a faster release, i.e. the concentration of the active ingredient in the serum or plasma increases faster than after administration of a solid dosage form (rapid onset), even if the solid dosage form is qualified as immediate release dosage form (IR). Such rapid onset is particularly desirable in the treatment of pain, since pain relief is to be achieved as fast as possible.

Preferably, the dosage form according to the invention is adapted for administration once daily, twice daily, thrice daily, four times daily, five times daily, six times daily or even more frequently.

In a preferred embodiment the dosage form according to the invention is adapted for administration to pediatric patients. For the purpose of the specification, pediatric patients preferably encompass infants, children, and adolescents. Preferably the upper age limit of such patients is 12, 13, 14, 15, 16, 17, 18, 19, 20 or 21.

In this regard the surprising preservative properties of tapentadol are even more beneficial, as the drug approval authorities have set stricter standards as to the presence of preservative in medicaments for pediatric patients. Further, as tapentadol is suitable for treating pain in patients suffering from serious diseases, e.g. for treating cancer pain, such patients including pediatric patients are usually simultaneously treated with other medicaments, e.g. chemotherapeutics, that have severe side effects. Under these circumstances, it is even more desirable to not expose such pediatric patients to preservatives, if avoidable.

A further aspect of the invention relates to the pharmaceutical composition according to the invention as described above or the pharmaceutical dosage form according to the invention as described above for use in the treatment of pain.

A still further aspect of the invention relates to the use of tapentadol for the manufacture of the pharmaceutical composition according to the invention as described above or of the pharmaceutical dosage form according to the invention as described above for the treatment of pain.

A yet further aspect of the invention relates to a method for the treatment of pain comprising the oral administration of the pharmaceutical composition according to the invention as described above or of the pharmaceutical dosage form according to the invention as described above to a subject in need thereof.

Preferably, the pain is selected from the group consisting of inflammatory pain, neuropathic pain, acute pain, chronic pain, visceral pain, migraine pain and cancer pain.

Another aspect of the invention relates to the use of tapentadol or a physiologically acceptable salt thereof as preservative.

EXAMPLES

The following examples further illustrate the invention but are not to be construed as limiting its scope.

Example 1

Determination of Antimicrobial Effective Concentration of Tapentadol Hydrochloride It has been revealed in initial studies that tapentadol hydrochloride at a concentration of 10 mg/mL free base exhibits a high antimicrobial activity and a high activity against yeast. The activity against mold (*Aspergillus niger*) is lower but still within the limits of the requirements of the Pharm. Eur. The activity of tapentadol hydrochloride against *Aspergillus niger* has been evaluated at lower drug concentrations and at pH 4.0 and 5.0 in formulations containing citric acid as buffer system and hydrochloric acid and sodium hydroxide to adjust the pH.

Results:

At pH 5 there is a better antimicrobial activity of tapentadol hydrochloride than at pH 4 after 14 and 28 days (see Table 1).

TABLE 1 log reduction *Aspergillus niger* 14 and 28 days after inoculation

| Ex. | tapentadol eq. (mg/mL) | pH | positive control, log | 14 days | 28 days |
|---|---|---|---|---|---|
| 1-1 | 2 | 4 | 5.2 | +0.1 | 0.1 |
| 1-2 | 2 | 5 | | 0.2 | 0.4 |
| 1-3 | 4 | 4 | | 0.3 | 0.4 |
| 1-4 | 4 | 5 | | 1.2 | 1.7 |
| 1-5 | 6 | 4 | | 0.8 | 1.2 |
| 1-6 | 6 | 5 | | 1.3 | 1.8 |
| 1-7 | 8 | 4 | | 1.2 | 1.6 |
| 1-8 | 8 | 5 | | 1.5 | 2.3 |
| 1-9 | 10 | 4 | | 1.5 | 1.9 |
| 1-10 | 10 | 5 | | 1.5 | 2.4 |

The requirements of Pharm. Eur. for oral solutions (log reduction of 1 after 14 and no increase after 28 days concerning mold *A. niger*) are met at pH 4 for tapentadol concentrations of equal or above 8 mg/mL and at pH 5 for concentrations equal or above to 4 mg/m L.

Conclusion:

At pH 4 minimal concentration of 8 mg/mL tapentadol is needed to meet the requirements of the Eur. Pharm. with regard to *Aspergillus niger*. There is a concentration limit of 4-8 mg/mL for antimicrobial effectiveness of tapentadol depending on the pH.

Example 2

Antimicrobial Robustness Testing of 20 mg/mL Tapentadol Oral Solution

The 20 mg/mL solution of tapentadol has been subjected to an antimicrobial robustness testing. As the drug substance tapentadol hydrochloride acts as the preservative, the antimicrobial activity of the formulation was determined at 100% and 90% of drug substance at three different pH levels (target, upper and lower limit-3.5-4-4.5). The following compositions of the formulation were used for the antimicrobial robustness testing (Table 2):

TABLE 2

Composition of the formulations (concentrations in mg/mL)

| | 100% drug substance | | | 90% drug substance | | |
|---|---|---|---|---|---|---|
| Example | 2-1 | 2-2 | 2-3 | 2-4 | 2-5 | 2-6 |
| tapentadol HCl | 23.3 | 23.3 | 23.3 | 20.97 | 20.97 | 20.97 |
| citric acid monohydrate | 2 | 2 | 2 | 2 | 2 | 2 |
| sucralose | 2.5 | 2.5 | 2.5 | 2.5 | 2.5 | 2.5 |
| raspberry flavor | 2 | 2 | 2 | 2 | 2 | 2 |
| NaOH ad pH | 4 | 3.5 | 4.5 | 4 | 3.5 | 4.5 |
| purified water q.s. ad | 1 mL | 1 mL | 1 mL | 1 mL | 1 mL | 1 mL |

The testing results revealed that the 20 mg/mL tapentadol oral solution has a high antibacterial effect and a high effect on inhibition of growth of *C. albicans* at all three tested pH levels, even at lower concentration of 90%. The effect on *A. niger* is lower but meets for both concentrations the requirements of the Pharm. Eur. and USP, showing the overall spectrum of tapentadol hydrochloride as a preservative.

Example 3

Antimicrobial Robustness Testing of 4 mg/mL Tapentadol Oral Solution (Lower Concentration of Sodium Benzoate)

The 4 mg/mL solution of tapentadol has also been subjected to an antimicrobial robustness testing. In this concentration the antimicrobial effect of the drug substance tapentadol hydrochloride is not sufficiently pronounced. Therefore, sodium benzoate has been used as a preservative in the formulation. The antimicrobial activity of the formulation was determined with 100% at target pH of 4 and with 80% of sodium benzoate at the pH limits of 3.5 and 4.5. The following compositions of the formulation were used for the antimicrobial robustness testing (Table 3).

TABLE 3

Composition of the formulations (concentrations in mg/mL)

| Example | 3-1 | 3-2 | 3-3 |
|---|---|---|---|
| tapentadol | 4.66 | 4.66 | 4.66 |
| sodium benzoate | 1.77 | 1.42 | 1.42 |
| citric acid monohydrate | 1.31 | 1.31 | 1.31 |
| sucralose | 2 | 2 | 2 |
| raspberry flavor | 2 | 2 | 2 |
| NaOH ad pH | 4.0 | 3.5 | 4.5 |
| purified water q.s. ad | 1 mL | 1 mL | 1 mL |

The testing results revealed that the 4 mg/mL tapentadol oral solution including 1.77 mg/mL sodium benzoate at target pH did not comply with the requirements of USP and Pharm. Eur. as an increase of *Ps. aeruginosa* from day 14 to day 28 has been observed.

Both formulations containing 80% preservative at the pH limits did comply, however, the obtained log reduction of 3.3 for *E. coli* is borderline.

Example 4

Antimicrobial Robustness Testing of 4 mg/mL Tapentadol Oral Solution (Higher Concentration of Sodium Benzoate)

Based on the obtained results the test was repeated using a formulation containing a higher preservative concentration of 2.36 mg/mL instead of 1.77 mg/mL sodium benzoate.

The above study of example 3 was repeated using a formulation of 4 mg/mL tapentadol and 2.36 mg/mL sodium benzoate (corresponding to 2 mg/mL benzoic acid). The antimicrobial activity of the formulation was determined with 100% at target pH of 4 and with 80% of sodium benzoate at the pH limits of 3.5 and 4.5. The following compositions of the formulation were used for the antimicrobial robustness testing (Table 4).

TABLE 4

Composition of the formulations (concentrations in mg/mL)

| Example | 4-1 | 4-2 | 4-3 |
|---|---|---|---|
| tapentadol | 4.66 | 4.66 | 4.66 |
| sodium benzoate | 2.36 | 1.89 | 1.89 |
| citric acid monohydrate | 1.7 | 1.7 | 1.7 |
| sucralose | 2 | 2 | 2 |
| raspberry flavor | 2 | 2 | 2 |
| NaOH ad pH | 4.0 | 3.5 | 4.5 |
| purified water q.s. ad | 1 mL | 1 mL | 1 mL |

The testing results revealed that all requirements from USP and Pharm. Eur. are fulfilled at target pH 4 and 100% sodium benzoate as well as for the other two formulations (pH limits at 80% sodium benzoate). Therefore, it can be concluded that 2.36 mg/mL sodium benzoate (corresponding to 2 mg/mL benzoic acid) is sufficient to provide antimicrobial efficacy for a 4 mg/mL tapentadol hydrochloride oral solution.

Example 5

In Use Stability Study with 20 mg/mL Tapentadol Oral Solution

For oral solution of tapentadol intended to be used as a multiple dosed form, an in-use stability study was performed with the focus on microbial stability. Therefore, during a period of 4 weeks approx. 1 mL of product was taken out 2 times on every working day in a non-controlled environment simulating the home conditions for patients. The test was performed on a total amount of 10 bottles. The solution was removed in a representative way (by dosing pipette) and the bottles were stored at room temperature after each removal. After the period of 4 weeks, a microbial count was performed on the residual solution of all tested bottles.

No microbial growth was observed for all bottles showing the overall good antimicrobial properties of tapentadol hydrochloride in a 20 mg/mL oral solution. It could be demonstrated that the formulation shows a sufficient antimicrobial effect coming from the incorporated drug substance.

Example 6

Screening Chemical Stability of 10 mg/mL Tapentadol Oral Solution

Chemical properties of a preliminary formulation containing tapentadol hydrochloride in the concentration of 10 mg/mL have been evaluated at different temperatures over a storage period of 6 months. As preservatives sodium benzoate was used in the one formulation approach, whereas methyl- and propyl parabens were used in a separate formulation approach.

Results:

After 1, 3 and 6 months at room temperature (25° C.) and high temperature (50° C.) the 10 mg/mL solution was evaluated with regard to the parameters assay of API tapentadol, degradation products as well as assay of the preservatives. The API assay remains stable within the 6 months storage duration. For the parabene formulation a degradation product was observed after 3 months with increased level at higher temperature.

Conclusion:

The formulation containing sodium benzoate showed less degradation products compared with the parabens formulation. Therefore, sodium benzoate was used as selected preservative for further development.

Example 7

Chemical Stability of 4 and 20 mg/mL Tapentadol Oral Solution

To investigate the chemical stability of tapentadol oral solutions in different concentrations (4 and 20 mg/mL), stability studies were performed over 3 months evaluating the following parameters appearance, assay of tapentadol, degradation, assay preservative (only for the 4 mg/mL formulation) and pH at 25° C./60% RH, 40° C./75% RH and 50° C. In addition, for the 4 mg/mL solution 2 weeks cycling studies (from −15° C. to 30° C. as well as from 5° C. to 40° C.) were performed.

Results:

No stability trends for both formulations (4 and 20 mg/mL) of tapentadol oral solution independent on the used flavor (raspberry or masking flavor) are obvious after 3 months storage time showing the good stability of the API tapentadol hydrochloride in solution.

Example 8

Antimicrobial Effect of Tapentadol at pH 3 and pH 8

A tapentadol solution with a concentration of 15 mg/mL tapentadol (free base) was prepared. The pH-value was adjusted to the target value of 3 or 8 using citric acid and 1N NaOH solution, respectively. No additional buffer system was added. To ensure the placebo solution shows no antimicrobial effect itself, a placebo solution pH 8 was prepared, with focus on the same pH-value, even though a different amount of 1N NaOH solution was used for pH adjustment.

The formulations were prepared, filled in glass bottles and sterilized in an autoclave for 30 min at 121° C. and 2 bars. The sterilized glass bottles were spiked with *Staphylococcus aureus* (*Staph. aureus*), *Pseudomonas aeruginosa* (*Ps. aerouginosa*), *Aspergillus niger* (*Asp. niger*) and *Candida albicans* for the test "Efficacy of antimicrobial preservation" on the basis of Ph. Eur. 6.6 monograph 5.1.3.

The Ph. Eur. test acceptance criteria for parenteral preparations are given in Table (NI=no increase, NR=no recover). The A criteria express the recommended efficacy to be achieved, in justified cases where the A criteria cannot be attained for example for reasons of an increased risk of adverse reaction, the B criteria must be satisfied. To reduce the amount of experiments for this first set up of pH-value experiments, the test points at 6 and 24 hours were replaced by a test point at 30 min (table 5).

TABLE 5

Acceptance criteria for parenteral preparations for "Efficacy of antimicrobial preservation" (Ph. Eur.) Log reduction

| | Test criteria | 6 h | 24 h | 7 d | 14 d | 28 d |
|---|---|---|---|---|---|---|
| Bacteria | A | 2 | 3 | — | — | NR |
| | B | — | 1 | 3 | — | NI |
| Fungi | A | — | — | 2 | — | NI |
| | B | — | — | — | 1 | NI |

The results for the microbial testing of the solutions are given for each bacteria/fungi in Tables 6 to 9.

TABLE 6

Microbial growth of Staph. aureus

| Microbial count | Placebo pH 8 | Tapentadol pH 8 | Tapentadol pH 3 |
|---|---|---|---|
| Spiked amount of bacteria/fungi | 7.4 × 10$^5$ | 1.7 × 10$^6$ | 1.6 × 10$^6$ |
| 30 min | 8.3 × 10$^5$ | 8 × 10$^5$ | 2.5 × 10$^6$ |
| 7 days | 2.8 × 10$^5$ | <×10$^2$ | 2.3 × 10$^3$ |
| 14 days | not tested | <×10$^2$ | <×10$^2$ |
| 28 days | not tested | <×10$^2$ | <×10$^1$ |
| Test criteria A | failed | passed | passed |
| Test criteria B | failed | passed | passed |

TABLE 7

Microbial growth of Ps. aeruginosa

| Microbial count | Placebo pH 8 | Tapentadol pH 8 | Tapentadol pH 3 |
|---|---|---|---|
| Spiked amount of bacteria/fungi | 1.4 × 10$^6$ | 1.7 × 10$^6$ | 1.6 × 10$^6$ |
| 30 min | 1.6 × 10$^6$ | <×10$^4$ | 4.5 × 10$^5$ |
| 7 days | 8.8 × 10$^6$ | <×10$^2$ | 2 × 10$^3$ |
| 14 days | not tested | <×10$^2$ | <×10$^2$ |
| 28 days | not tested | <×10$^2$ | <×10$^2$ |
| Test criteria A | failed | passed | passed |
| Test criteria B | failed | passed | passed |

TABLE 8

Microbial growth of Asp. niger

| Microbial count | Placebo pH 8 | Tapentadol pH 8 | Tapentadol pH 3 |
|---|---|---|---|
| Spiked amount of bacteria/fungi | 4.2 × 10$^5$ | 5.4 × 10$^5$ | 3.9 × 10$^5$ |
| 30 min | 4.3 × 10$^5$ | 6 × 10$^5$ | 4.5 × 10$^5$ |
| 7 days | 6.3 × 10$^5$ | 4.5 × 10$^2$ | 8 × 10$^4$ |
| 14 days | not tested | 0.3 × 10$^2$ | 4.1 × 10$^5$ |
| 28 days | not tested | 1.8 × 10$^1$ | 4.5 × 10$^5$ |
| Test criteria A | failed | passed | failed |
| Test criteria B | failed | passed | failed |

TABLE 9

Microbial growth of Candida albicans

| Microbial count | Placebo pH 8 | Tapentadol pH 8 | Tapentadol pH 3 |
|---|---|---|---|
| Spiked amount of bacteria/fungi | 2 × 10$^5$ | 1.7 × 10$^5$ | 2.4 × 10$^5$ |
| 30 min | 2.5 × 10$^5$ | <×10$^4$ | 2 × 10$^5$ |
| 7 days | 3.4 × 10$^6$ | <×10$^2$ | 1.3 × 10$^3$ |
| 14 days | not tested | <×10$^2$ | 1.8 × 10$^3$ |
| 28 days | not tested | <×10$^2$ | 2.5 × 10$^3$ |
| Test criteria A | failed | passed | failed |
| Test criteria B | failed | passed | failed |

In the absence of additional preservatives, the tapentadol solution pH 3 is not sufficiently preserved according to Ph. Eur. (crit. A and B) for *Asp. niger* and *Cand. albicans*, whereas the tapentadol solution pH 8 passed the crit. A and B for all tested bacteria and funghi. The placebo pH 8 solution shows no preservative effect of the solution itself, so that the antimicrobial effect of the formulation containing tapentadol HCl is a consequence of the added amount of tapentadol HCl. Considering this results a clear dependency of the pH-value on the preserving effect of the tapentadol HCl solution could be shown.

The tapentadol HCl solution with a higher pH value of 8 has an improved antimicrobial effect compared to the pH 3 solution, so a clear dependency of the pH-value of the solution on the preserving effect of tapentadol was found.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. An aqueous pharmaceutical composition comprising:
   (a) water;
   (b) a buffer;
   (c) tapentadol or a physiologically acceptable salt thereof; and
   (d) a preservative,
   wherein:
   the aqueous pharmaceutical composition is orally administrable;
   the aqueous pharmaceutical composition is buffered to a pH value of at least 3.0 and at most 6.5;
   the preservative is present in the composition in an amount insufficient to preserve the composition according to Ph. Eur. in the absence of the tapentadol or the physiologically acceptable salt thereof; and
   the aqueous pharmaceutical composition is a multiple dosed form.

2. The aqueous pharmaceutical composition according to claim 1, wherein the tapentadol or a physiologically acceptable salt thereof is present at a concentration of 50 mg/mL or less, based on the total volume of the aqueous pharmaceutical composition.

3. The aqueous pharmaceutical composition according to claim 1, wherein the aqueous pharmaceutical composition exhibits a shelf-life under accelerated storage conditions of at least 3 months.

4. The aqueous pharmaceutical composition according to claim 1, wherein the aqueous pharmaceutical composition is selected from the group consisting of a syrup, a drop, a solution, a dispersion, a suspension, and an emulsion.

5. The aqueous pharmaceutical composition according to claim 1, wherein the aqueous pharmaceutical composition is selected from the group consisting of an oral solution, an oral gel, a suspension, and an emulsion.

6. The aqueous pharmaceutical composition according to claim 1, wherein the aqueous pharmaceutical composition is adapted for administration to a pediatric patient.

7. A method of treating pain in a subject in need thereof, the method comprising administering to the subject a pharmaceutically effective amount of an aqueous pharmaceutical composition according to claim 1.

8. The method according to claim 7, wherein the pain is selected from the group consisting of acute pain and chronic pain.

9. The aqueous pharmaceutical composition according to claim 1, wherein the aqueous pharmaceutical composition exhibits an in-use stability under ambient conditions of at least 4 weeks.

10. The aqueous pharmaceutical composition according to claim 1, wherein the water is present at at least 20 wt.-% by weight of the aqueous pharmaceutical composition.

11. The aqueous pharmaceutical composition according to claim 1, wherein the aqueous pharmaceutical composition does not comprise sodium chloride.

12. The aqueous pharmaceutical composition according to claim 1, wherein the buffer is a pH buffer.

13. The aqueous pharmaceutical composition according to claim 1, wherein the buffer comprises a pH buffer system derived from an organic acid.

* * * * *